United States Patent [19]
Chung et al.

[11] Patent Number: 5,283,056
[45] Date of Patent: Feb. 1, 1994

[54] TRANSPARENT OIL-IN-WATER MICROEMULSION FLAVOR OR FRAGRANCE CONCENTRATE, PROCESS FOR PREPARING SAME, MOUTHWASH OR PERFUME COMPOSITION CONTAINING SAID TRANSPARENT MICROEMULSION CONCENTRATE, AND PROCESS FOR PREPARING SAME

[75] Inventors: Siew L. Chung, Red Bank; Chee-Tack Tan, Middletown, both of N.J.; Ivan M. Tuhill, Clare, United Kingdom; Lewis G. Scharpf, Fair Haven, N.J.

[73] Assignee: International Flavors & Fragrances Inc., New York, N.Y.

[21] Appl. No.: 84,610

[22] Filed: Jul. 1, 1993

[51] Int. Cl.$^5$ .................... A61K 7/16; A61K 7/26; A61K 7/46; A61K 9/10
[52] U.S. Cl. .................... 424/49; 252/174.11; 252/310; 424/58; 426/650; 426/651; 512/1; 512/2; 512/3; 512/4
[58] Field of Search ................ 424/49–58; 512/1–4; 426/650, 651; 252/310, 174.11

[56] References Cited

U.S. PATENT DOCUMENTS

| | | | |
|---|---|---|---|
| 4,146,499 | 3/1979 | Rosano | 252/186 |
| 4,568,480 | 2/1986 | Thir et al. | 252/312 |
| 4,752,481 | 6/1988 | Dokuzovic | 426/3 |
| 4,835,002 | 5/1989 | Wolf et al. | 426/590 |
| 4,842,766 | 6/1989 | Blehm et al. | 252/309 |
| 4,919,918 | 4/1990 | Cole et al. | 424/49 |
| 4,923,685 | 5/1990 | Wuelknitz et al. | 424/54 |
| 4,971,788 | 11/1990 | Tabibi et al. | 424/49 |
| 4,992,259 | 2/1991 | Schiraldi et al. | 424/49 |
| 5,045,337 | 9/1991 | El-Nokaly et al. | 426/602 |
| 5,076,954 | 12/1991 | Loth et al. | 252/122 |
| 5,082,584 | 1/1992 | Loth et al. | 252/122 |
| 5,108,643 | 4/1992 | Loth et al. | 252/174.11 |
| 5,130,122 | 7/1992 | Tabibi et al. | 424/49 |
| 5,143,720 | 9/1992 | Lopes | 424/55 |
| 5,145,664 | 9/1992 | Thompson | 424/49 |
| 5,156,766 | 10/1992 | Behan et al. | 252/312 |
| 5,160,669 | 11/1992 | Wallach et al. | 264/4.3 |
| 5,188,822 | 2/1993 | Viccaro et al. | 424/52 |
| 5,190,915 | 3/1993 | Behan et al. | 512/2 |

FOREIGN PATENT DOCUMENTS

| | | | |
|---|---|---|---|
| 2019719 | 12/1991 | Canada . | |
| 316726 | 5/1989 | European Pat. Off. | C11D 3/18 |
| 368146 | 5/1990 | European Pat. Off. | C11D 3/48 |
| 516508 | 12/1992 | European Pat. Off. | A61K 7/46 |
| 9209260 | 6/1992 | PCT Int'l Appl. . | |
| 1428945 | 3/1976 | United Kingdom . | |

OTHER PUBLICATIONS

Fribert and Venable, "Microemulsions", Chapter 4, of the Encyclopedia of Emulsion Technology, vol. I, Basic Theory, Edited by Paul Becher, Published by Marcel Dekker, N.Y., 1983, pp. 287 to 336.

Blakeway, "Water-Based Perfumes Cosmetics & Toiletries", vol. 108, Jun. 1993, pp. 59, 60 and 61 (originally published in Perfumer & Flavorist, Jan./Feb. 1993, vol. 18, No. 1).

*Primary Examiner*—Shep K. Rose
*Attorney, Agent, or Firm*—Arthur L. Liberman

[57] ABSTRACT

Described is a stable transparent oil-in-water microemulsion concentrate consisting essentially of:
 (i) water;
 (ii) one or more hydrophobic flavor or fragrance oils; and
 (iii) one or more surfactants wherein the mixing ratio of the water, oil and surfactant is, referring to FIG. 1A, within the range surrounded by the lines connecting points A, B and C of FIG. 1A. Also described is a process for preparing such transparent microemulsion compositions. Also described is a mouthwash containing said transparent microemulsion compositions and a process for preparing same. Also described is a perfume composition containing said transparent microemulsion compositions and the process for preparing same.

9 Claims, 8 Drawing Sheets

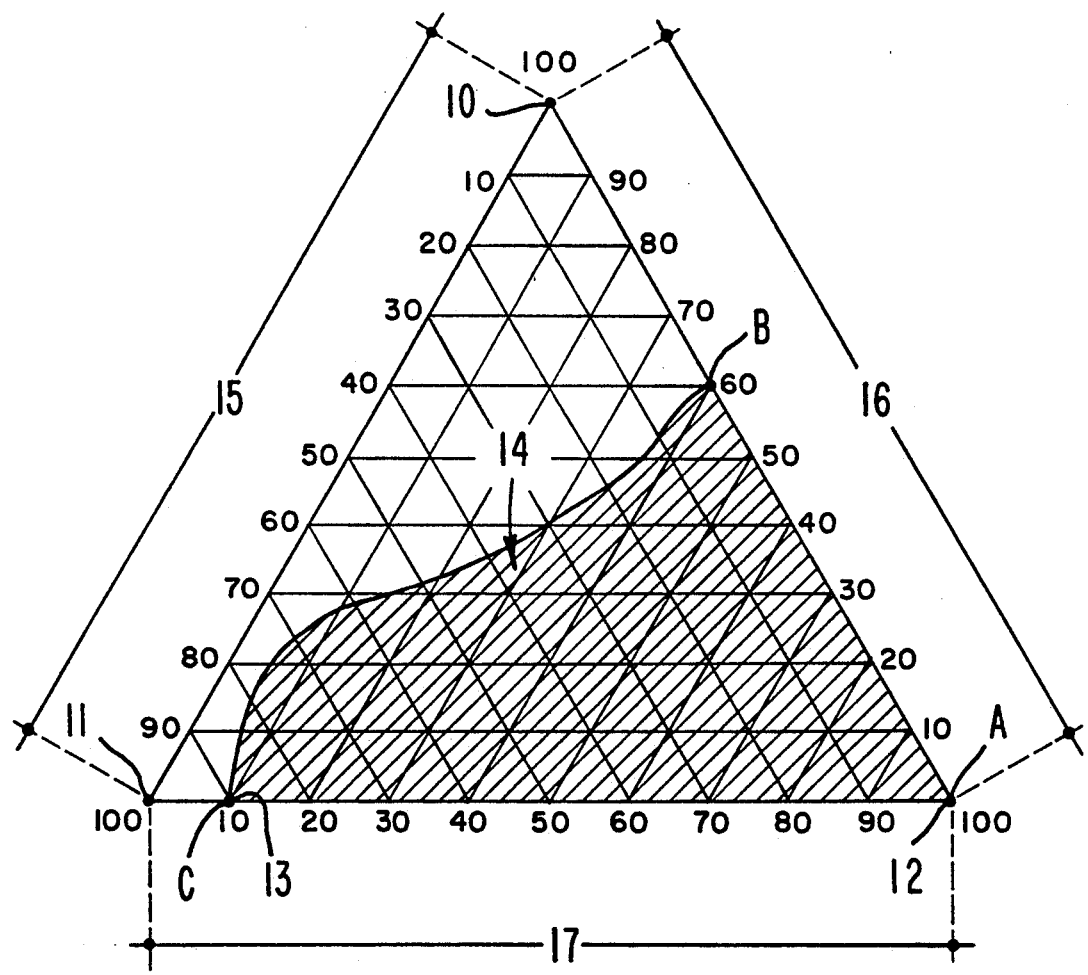
FIG.1-A

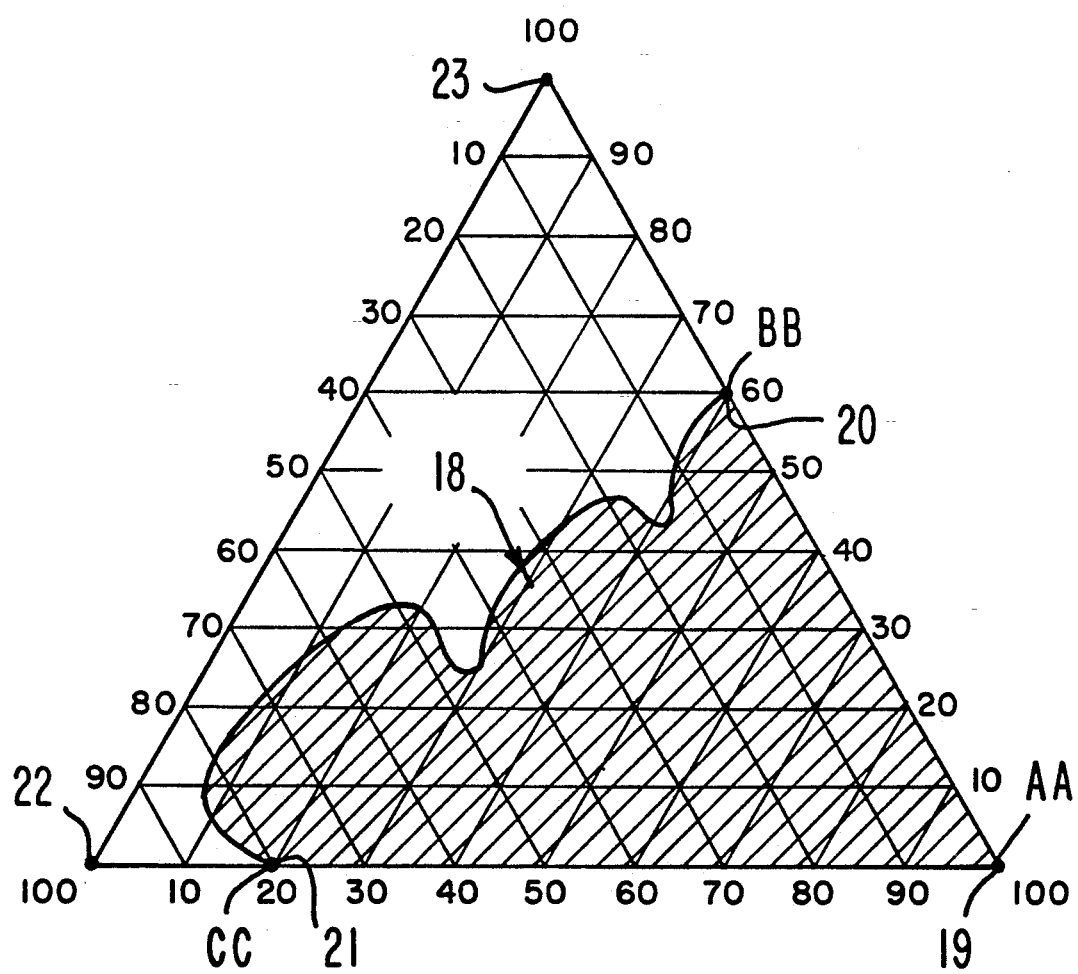
FIG.I-B

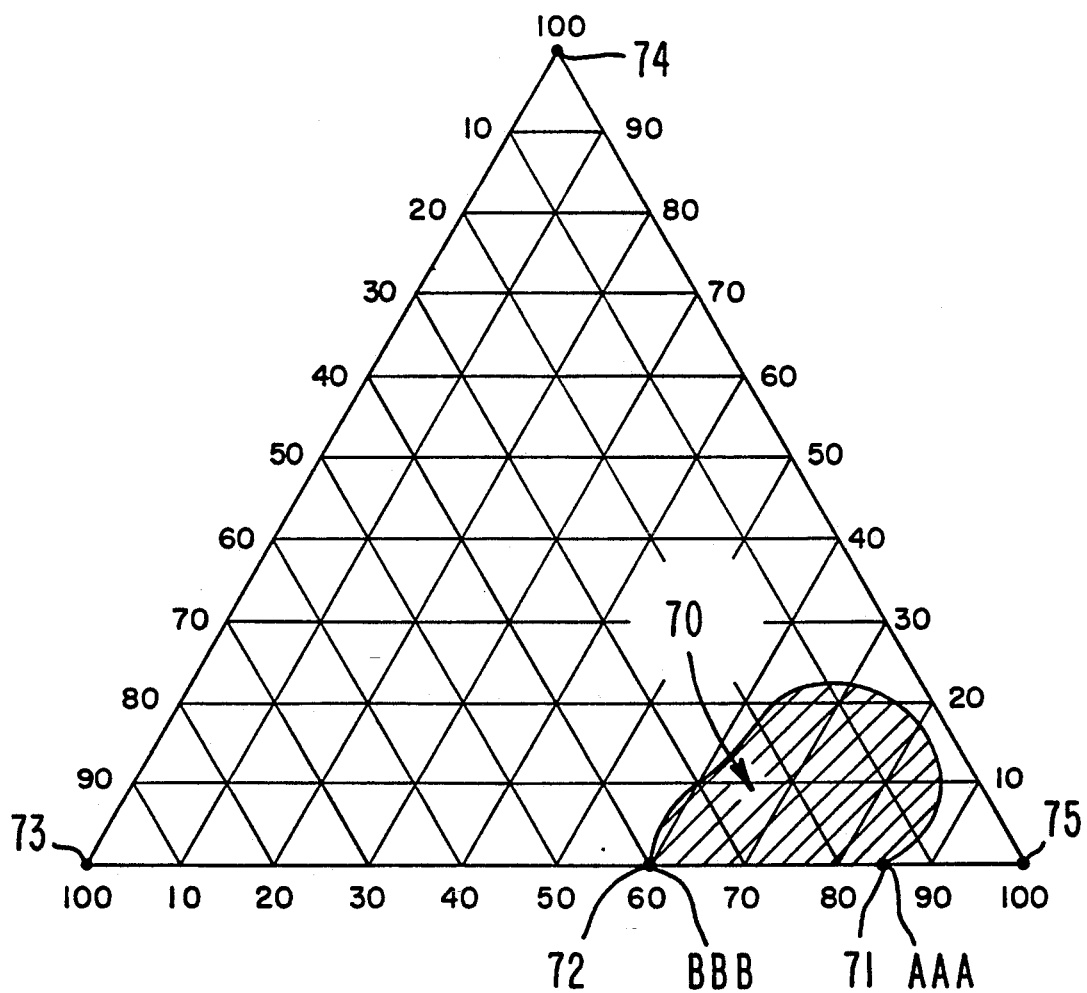

TRANSPARENT OIL-IN-WATER MICROEMULSION FLAVOR OR FRAGRANCE CONCENTRATE, PROCESS FOR PREPARING SAME, MOUTHWASH OR PERFUME COMPOSITION CONTAINING SAID TRANSPARENT MICROEMULSION CONCENTRATE, AND PROCESS FOR PREPARING SAME

BACKGROUND OF THE INVENTION

Our invention relates to stable transparent oil-in-water microemulsion concentrates consisting essentially of:
(i) water;
(ii) one or more hydrophobic flavor or fragrance oils; and
(iii) one or more surfactants as well as a process for preparing such transparent microemulsion compositions, mouthwash compositions containing such transparent microemulsion compositions, and perfume compositions containing such transparent microemulsion compositions.

The concept of the microemulsion was introduced by Schulman and Montague, Ann. New York Academy of Science, 1961, Volume 92, page 366. Becher, American Chemical Society Symposium Series 448, ACS, Washington, D.C., 1991 contains two chapters covering microemulsions in foods: Chapter 1, El- Nokaly, et al and Chapter 2, Friberg, et al. The microemulsion system typically contains relatively large amounts of oil and water along with a surfactant and cosurfactant except in the case of certain hydrophobic surfactants where no cosurfactant may be required. These systems are indicated in the prior art to form spontaneously as a result of contact between the several components.

The most characteristic difference between an emulsion and a microemulsion is the appearance of the microemulsion an the emulsion. An emulsion is turbid while the microemulsion is transparent.

Rosano, U.S. Pat. No. 4,146,499 issued on Mar. 27, 1979 discloses a method for the preparation of oil-in-water microemulsions via a four-step process: (1) a surfactant is selected which is just barely soluble in the oil phase; (2) the surfactant thus selected is dissolved in the oil to be emulsified in an amount effective to yield a fine emulsion of the emulsified oil in an aqueous phase; (3) the oil, together with its dissolved surfactant is added to the water phase and shaken or stirred; and (4) finally there is provided a second surfactant in the water phase which is somewhat more soluble in water than the first surfactant to produce a substantially clear microemulsion of oil in water. Wolf, et al, U.S. Pat. No. 4,835,002 issued on May 30, 1989 discloses microemulsions of edible oils in a matrix of water and certain alcohols which are prepared using certain edible surfactants for use in various products such as beverages. El-Nokaly, et al, U.S. Pat. No. 5,045,337 issued on Sep. 3, 1991 discloses microemulsions which are thermodynamically stable, clear and homogeneous which are made from a polar solvent, a specific polyglycerol mono, diester and a lipid. El-Nokaly, et al discloses that these microemulsions are edible, have good flavor and can be used to disperse water soluble nutrients, vitamins, flavors and flavor precursors in oils. The polyglycerol mono diester in El-Nokaly, et al consists of a mixture of mono and diesters of branched or unsaturated fatty acids having from 12 to 24 carbon atoms and a polyglycerol mixture consisting of 0% to 10% monoglycerol and other polyglycerols, 30% of less diglycerol, 25% to 50% triglycerol, 15% to 50% tetraglycerol. Tabibi, et al, U.S. Pat. No. 5,130,122 issued on Jul. 14, 1992 discloses oral cavity and dental products prepared by microemulsifying an adsorptive oil in an aqueous medium to produce uniform submicron sized droplets. It is disclosed by Tabibi, et al that the products disclosed therein avoid the generally unaesthetic, oily, and unpleasant taste problems of previous similar products.

Nothing in the prior art discloses or implies a high flavor or fragrance loading, e.g., 25% flavor or fragrance oil in a microemulsion which has unexpectedly and advantageously high stability yet is free of lower alkanols, e.g., ethyl alcohol or contains less than about 1% of lower alkanols, e.g., ethyl alcohol.

SUMMARY OF THE INVENTION AND OBJECTS OF THE INVENTION

Our invention relates to an oil-in-water microemulsion prepared from a flavor or fragrance oil, water and a surfactant with or without a co-surfactant to stabilize the microemulsion.

It is an object of our invention to produce an oil-in-water microemulsion that is transparent and stable. A second objective of our invention is to prepare a mouthwash composition or fragrance composition containing little or no lower alkanol such as ethyl alcohol but will still maintain its stability and yield a transparent product.

The foregoing objects can be achieved by forming a stable oil-in-water microemulsion flavor or fragrance concentrate consisting of:
(i) water;
(ii) one or more hydrophobic flavor oils; and
(iii) one or more surfactants wherein the mixing ratio of water, oil and surfactant is, referring to FIG. 1A within the range surrounded by the lines connecting point "A" (100% of surfactant), point "B" (60% flavor of fragrance oil) and point "C" (90% water), excluding the points "A", "B" and "C", the line connecting points "A" and "B", the line connecting points "A" and "C" and the curve connecting points "B" and "C" wherein all of said three components are present. The curve connecting points "B" and "C" can be described by the mathematical model:

$$z = \alpha x + \beta y + \alpha' x^2 + \beta' y^2 + \alpha'' x^3 + \beta'' y^2 + \gamma xy + \gamma' x^2 y + \gamma'' xy^2$$

wherein z is the percent flavor or fragrance oil; x is the percent water and y is the percent surfactant; and wherein the terms:

$\alpha$
$\alpha'$
$\alpha''$
$\beta$
$\beta'$
$\beta''$
$\gamma$
$\gamma'$
and
$\gamma''$ are constants.

The flavor or fragrance oil used in our invention may, in fact, may be one or a mixture of oils soluble in one another. Thus, for example, the fragrance oil may be a mixture of geranium oil and lavender oil. The flavor oil may be a mixture of peppermint oil and spearmint oil. When the oils are prepared for ultimately using same in a mouthwash, it is preferred that such oils give rise to a "freshening" effect in the mouth on use. Both the fragrance oil and the flavor oil are insoluble in water and are to be considered as the oil phase in the microemulsion where water is the continuous phase.

The surfactants useful in the practice of our invention include all surfactants useful for mouthwash and all surfactants useful in perfumes. Examples of such surfactants are as follows:

TWEEN®20 (Polyoxyethylene (20) Sorbitan Monolaurate) TWEEN® (is a Trademark of ICI Americas of Wilmington, Del. 19897);

TWEEN®40 (Polyoxyethylene (20) Sorbitan Monopalmitate);

TWEEN®60 (Polyoxyethylene (20) Sorbitan Monostearate);

TWEEN®80 (Polyoxyethylene (20) Sorbitan Mono-oleate);

CREMOPHOR® RH 40 (Ethoxy Hydrogenated Castor Oil) (CREMOPHOR® is a Trademark of BASF Aktiengesellschaft of D-6700 Ludwigshafen, Federal Republic of Germany);

CREMOPHOR®RH 60 (Ethoxy Hydrogenated Castor Oil);

GENAPOL® (Alcohol Polyglycol Ether) (GENAPOL® is a Trademark of Hoechst Aktiengesellschaft of D-6230 Frankfurt AM Main No. 80, Postfach 80, Federal Republic of Germany);

Sodium Lauryl Sulphate;

POLOXAMER®407 (also known as PLURONIC® F127 and PLURACARE® F127) (Ethylene oxide-propylene oxide block copolymer having the formula:

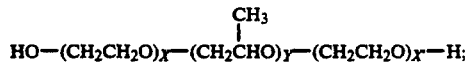

and an average molecular weight of 12,600) (POLOXAMER®, PLURONIC® and PLURACARE® are Trademarks of BASF Corporation of Parsippany, N.J. 07054);

SPAN®20 (Sorbitan Monolaurate) (SPAN® is a Trademark of ICI Americas of Wilmington, Del. 19897);

SPAN®40 (Sorbitan Monopalmitate);

SPAN®60 (Sorbitan Monostearate); and

SPAN®80 (Sorbitan Monooleate).

SPAN®s have the formula:

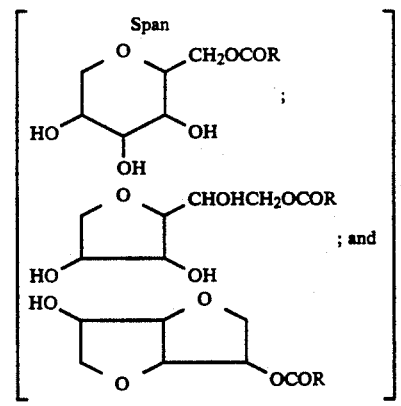

(a mixture wherein R is a fatty acid moiety. TWEEN®s are polyoxyethylene-substituted SPAN®s. Reference: The Merck Index, 8th Edition, Published by Merck & Company Inc., Rahway, N.J. 1968, at pages 848, 849 and 973.

The foregoing surfactants can be used taken alone or taken in combination of two or more.

The water phase can be pure water or may contain small amounts (e.g., less than 1%) of preservative, anti-microbial and humectant added when necessary. Such compounds are sodium benzoate, sodium or potassium propionate, potassium sorbate, glycerol and propylene glycol.

The microemulsion of our invention is prepared by following the shaded areas of the phase diagrams of FIGS. 1-7, inclusive using surfactant, flavor or fragrance oil and water as the components. The procedure is to mix flavor or fragrance oil first with surfactants; then add water. The resulting mixture is mixed for a short period of time (between from about 5 seconds up to about 10 minutes) depending on the property of the mixture. When the surfactant is in solid form or is highly viscous, the mixture is heated in order to ease the mixing. When a microemulsion is formed the mixture becomes transparent to white light.

For example, the acceptable mouthwash flavor microemulsion for clear mouthwash is one that also produces a clear solution in finished mouthwash which contains no or low alcohol content (that is, less than 1% ethyl alcohol).

The microemulsion of our invention preferably has a viscosity in the range of from about 70 up to about 18,000 centipoises at a temperature in the range of from 20° C. up to 30° C. and a refractive index in the range of from 1.4 up to 1.6 at a temperature in the range of from 20° C. up to 30° C. When formulating mouthwash formulations, the microemulsion flavor is present in the mouthwash from about 0.05% up to about 0.4%.

BRIEF DESCRIPTION OF THE DRAWINGS

FIG. 1A is a component ternary phase diagram of flavor or fragrance oil, surfactant and water showing in the shaded area the stable transparent oil and water microemulsion flavor or fragrance concentrate substantially in the absence of lower alkanols of our invention.

FIG. 1B is a more specific ternary phase diagram of the stable transparent oil in water microemulsion flavor or fragrance concentrate substantially in the absence of lower alkanols of our invention.

FIG. 7 is a more limited ternary phase diagram of the stable transparent oil in water microemulsion concentrates substantially in the absence of lower alkanols of our invention.

DETAILED DESCRIPTION OF THE DRAWINGS

Figure 2:
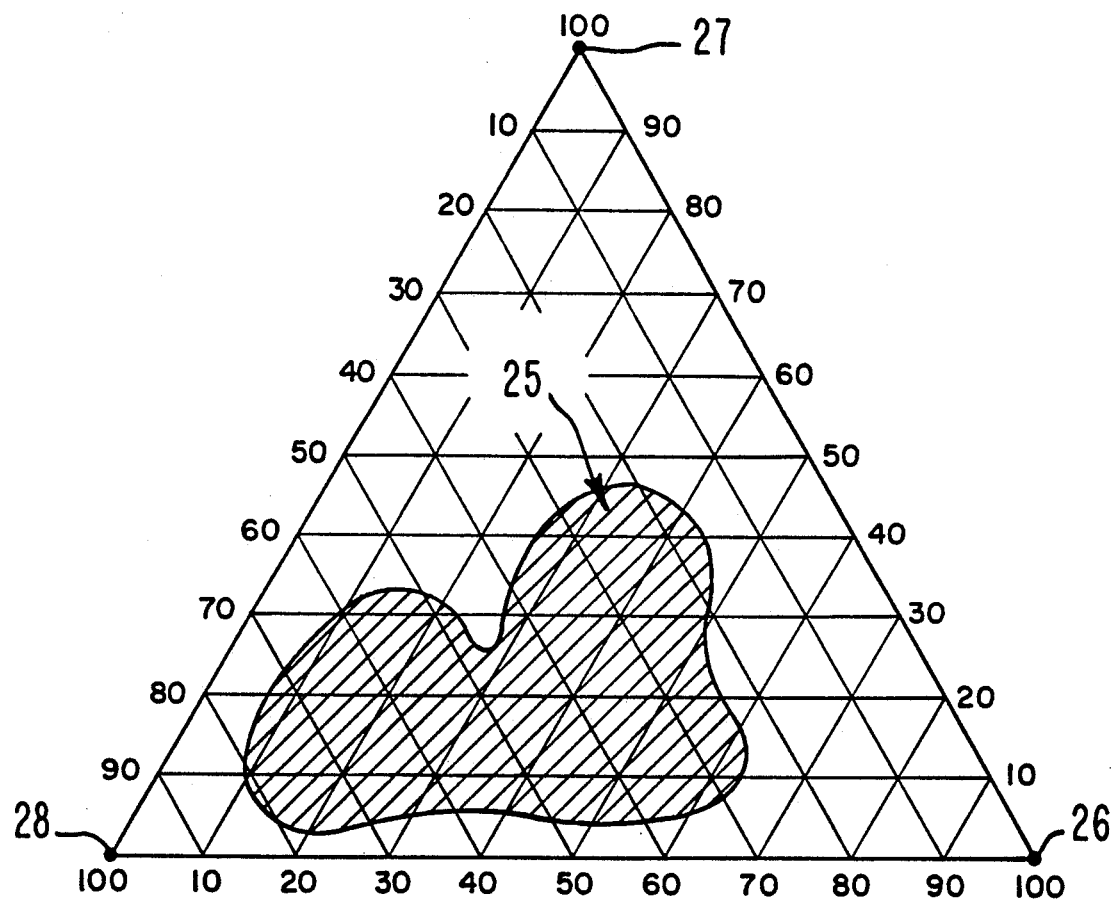
FIG. 2 is a more limited ternary phase diagram of the stable transparent oil in water microemulsion concentrates substantially in the absence of lower alkanols of our invention.

FIG. 1A is a ternary phase diagram of the stable transparent oil and water microemulsion flavor or fragrance concentrate of our invention which consists essentially of:
(i) water;
(ii) one or more hydrophoic flavor oils; and
(iii) one or more surfactants substantially in the absence of lower alkanols such as ethanol wherein the mixing ratio of water, oil and surfactant is referring to FIG. 1A within the range surrounded by the lines connecting point "A" indicated by reference numeral 12 (100% of surfactant), point "B" (60% flavor or fragrance oil) and point "C" indicated by reference numeral 13 (90% water) excluding the points "A", "B" and "C"; the line connecting points "A" and "B" (along the side indicated by reference numeral 16 of the ternary phase diagram) and the curve connecting points "B" and "C" wherein all three components are present. The point indicated by reference numeral 11 shows 100% water. The point indicated by reference numeral 10 shows 100% flavor or fragrance oil. The side of the diagram indicated by reference numeral 15 shows increasing values from 0% oil up to 100% oil and decreasing values of water from 100% water down to 0% water. The side indicated by reference numeral 17 shows increasing amounts of surfactant from 0 to 100% starting from point 11 and ending at point 12 and decreasing amounts of water from 100% down to 0% from point 11 to point 12.

Referring to FIG. 1B, the ternary phase diagram shows a more restricted phase envelope bonded by the curve from point "CC" to point "BB" and by the lines "BB"-"AA" and "AA"-"CC". The shaded area is indicated by the reference numeral 18 (compared with the shaded area of FIG. 1A indicated by reference numeral 14). The point "CC" is also indicated by reference numeral 21. The point "AA" is also indicated by reference numeral 19. One hundred percent flavor or fragrance oil is indicated by reference numeral 23. One hundred percent water is indicated by reference numeral 22. One hundred percent surfactant is indicated by reference numeral 19.

FIG. 2 is a ternary phase diagram of a specific system of the transparent microemulsion of our invention which is a stable transparent oil-in-water microemulsion flavor concentrate consisting essentially of:
(i) water;
(ii) a hydrophobic flavor oil; and
(iii) a mixture of surfactants substantially in the absence of lower alkanols. The point indicated by reference numeral 28 is for 100% of the mixture:
84.18% water;
0.02% sodium citrate;
15.0% sodium lauryl sulfate;
0.4% glycerine; and
0.4% propylene glycol.

The shaded area of the diagram indicated by reference numeral 25 is for the stable transparent oil-in-water microemulsion flavor concentrate area. The point indicated by reference numeral 27 is for 100% flavor oil. The point indicated by reference numeral 26 is for 100% detergent consisting of:
30% TWEEN ®20;
20% TWEEN ®80;
20% CREMOPHOR ® RH 40; and
30% CREMOPHOR ® RH 60.

Figure 3:
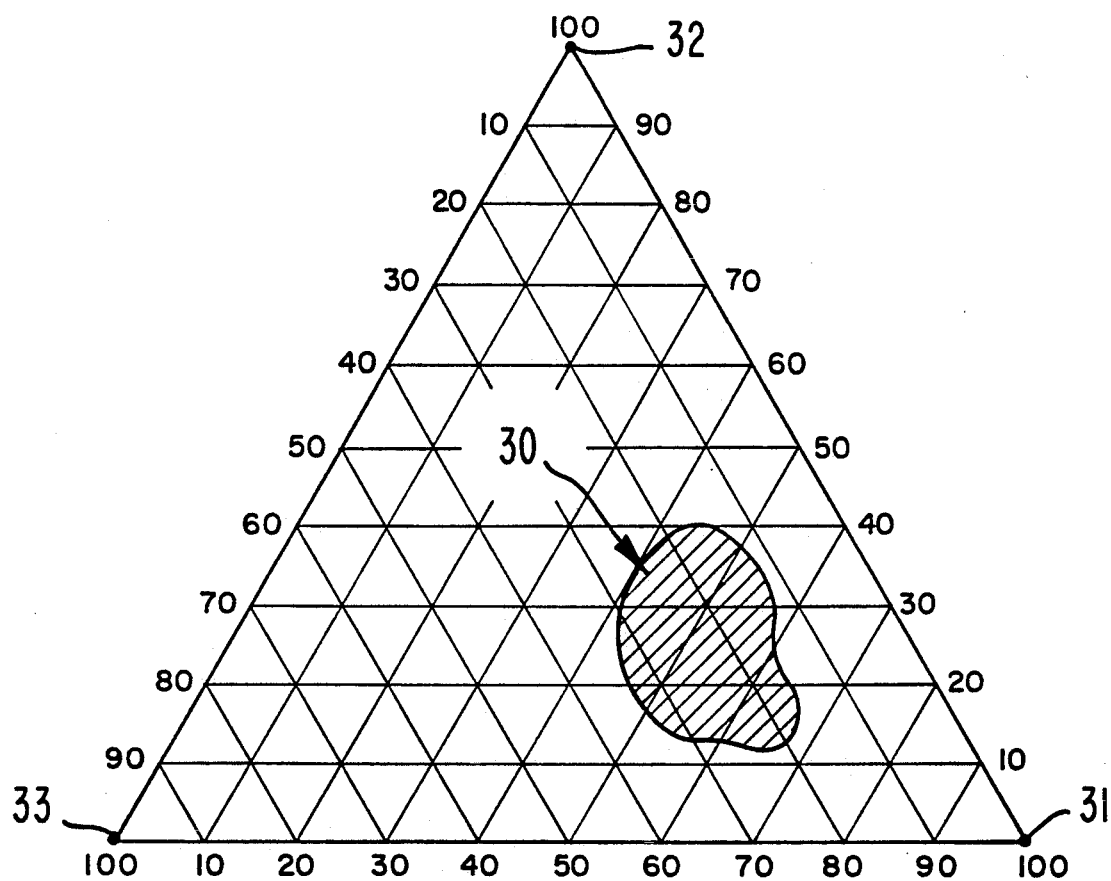
FIG. 3 is a more limited ternary phase diagram of the stable transparent oil in water microemulsion concentrates substantially in the absence of lower alkanols of our invention.

FIG. 3 is another ternary phase diagram which is even more definitive and covers stable transparent oil-in-water microemulsion flavor concentrates consisting essentially of:
(i) water;
(ii) a hydrophobic flavor oil; and
(iii) a surfactant.

The shaded area indicated by reference numeral 30 is the area of the phase diagram covering the microemulsion components of our invention. The point indicated by reference numeral 31 is for 100% detergent, in this case PLURONIC® F 127. The point indicated by reference numeral 33 is for 100% water. The point indicated by reference numeral 32 is for 100% flavor oil.

Figure 4:
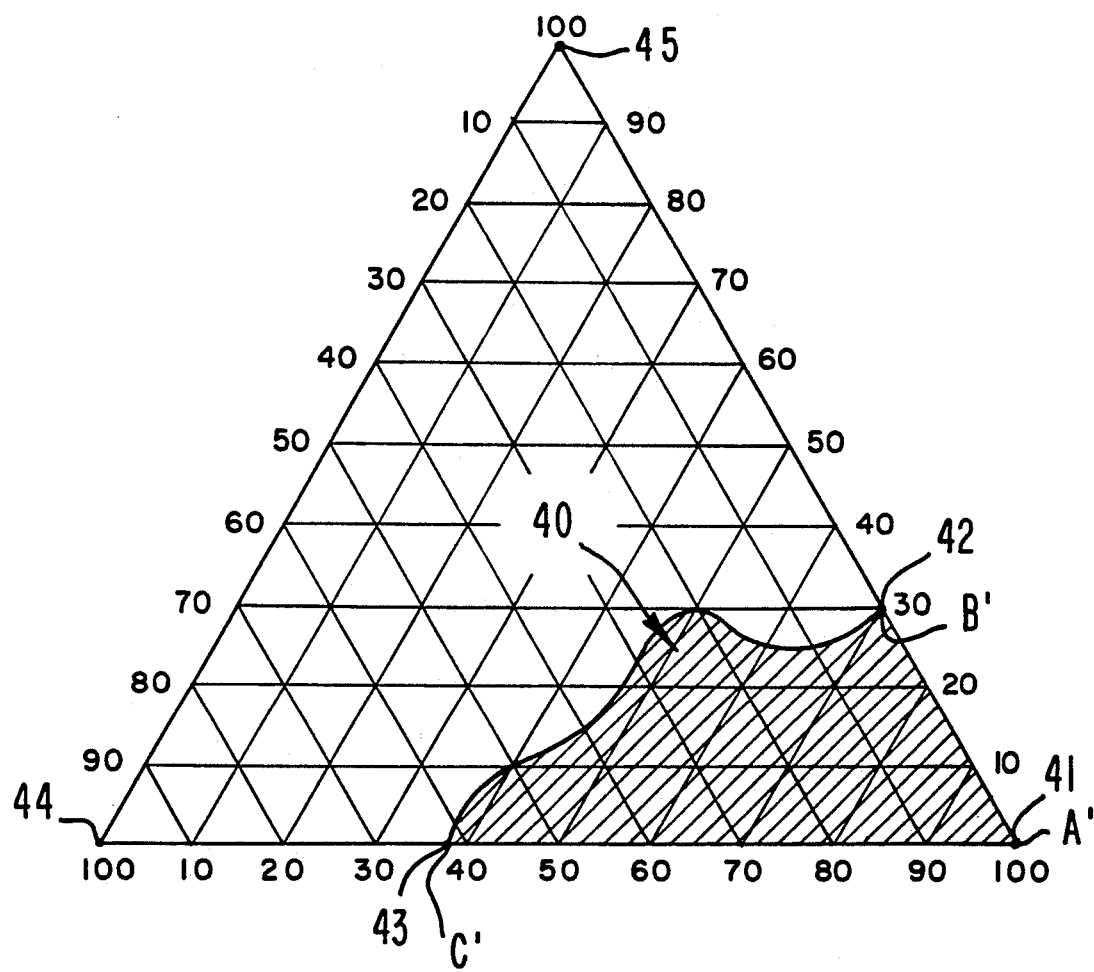
FIG. 4 is a more limited ternary phase diagram of the stable transparent oil in water microemulsion concentrates substantially in the absence of lower alkanols of our invention.

FIG. 4 is another ternary phase diagram showing a stable transparent oil-in-water microemulsion flavor concentrate consisting essentially of:
(i) water;
(ii) a hydrophobic flavor oil; and
(iii) a surfactant substantially in the absence of lower alkanols. The area which includes the components of our invention is indicated by reference numeral 40. The area is bounded by lines "A'", "C'" and "A'", "B'" and by the curve "B'", "C'". The ends of the curve at "C'" are indicated by reference numeral 43 and at "B'" are indicated by reference numeral 42. The point showing 100% surfactant in this case TWEEN ®20 is indicated by reference numeral 41. The point indicating 100% water is indicated by reference numeral 44. The point indicating 100% mouthwash flavor is indicated by reference numeral 45.

Figure 5:
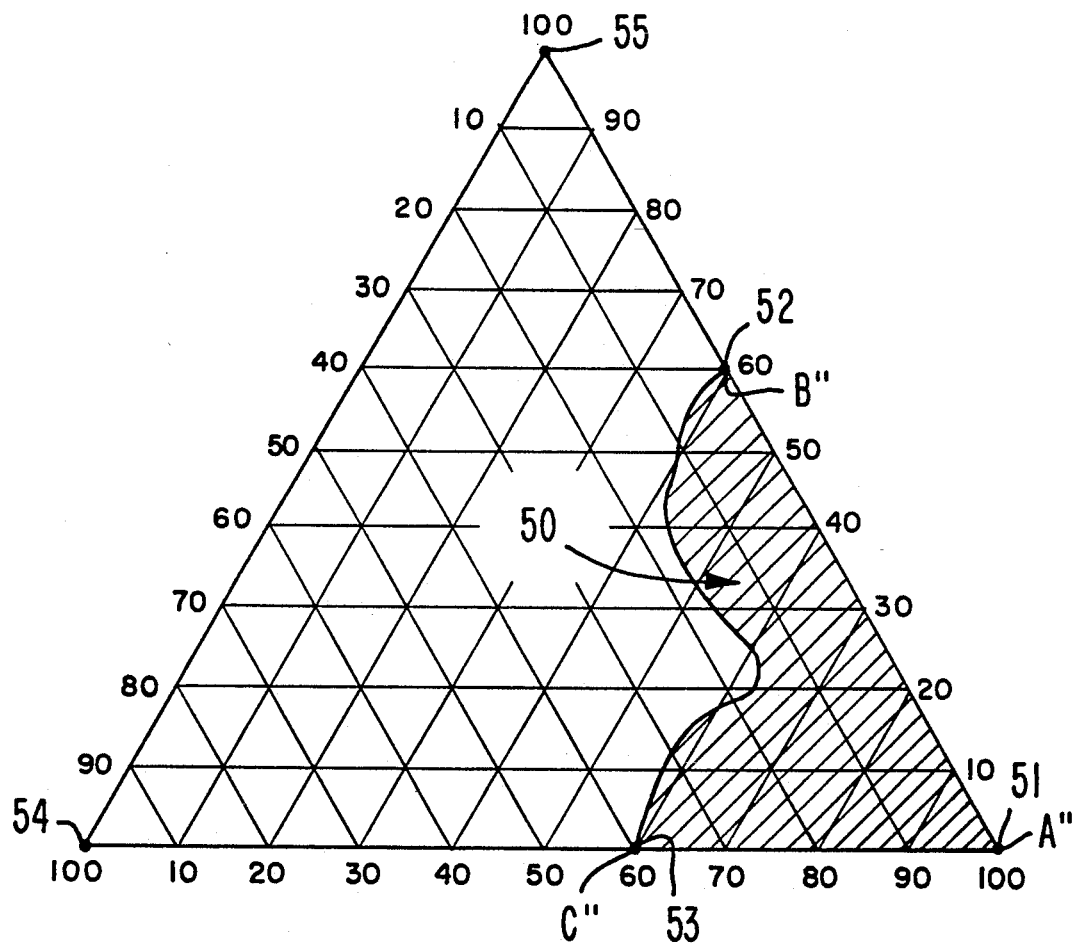
FIG. 5 is a more limited ternary phase diagram of the stable transparent oil in water microemulsion concentrates substantially in the absence of lower alkanols of our invention.

FIG. 5 is a ternary phase diagram for another transparent microemulsion flavor of our invention. The area indicated by reference numeral 50 is the area for the components of this aspect of our invention, boudded by lines "A''''"-"B''''" and "A''''"-"C''''" and by the curve "C''''"-"B''''". The ends of the curve at "B''''" are indicated by reference numeral 52 and at "C''''" are indicated by reference numeral 53. The point indicating 100% detergent, in this case TWEEN ®80, is indicated by reference numeral 51. The point indicating 100% water is indicated by reference numeral 54. The point showing 100% mouthwash flavor is indicated by reference numeral 55.

Figure 6:
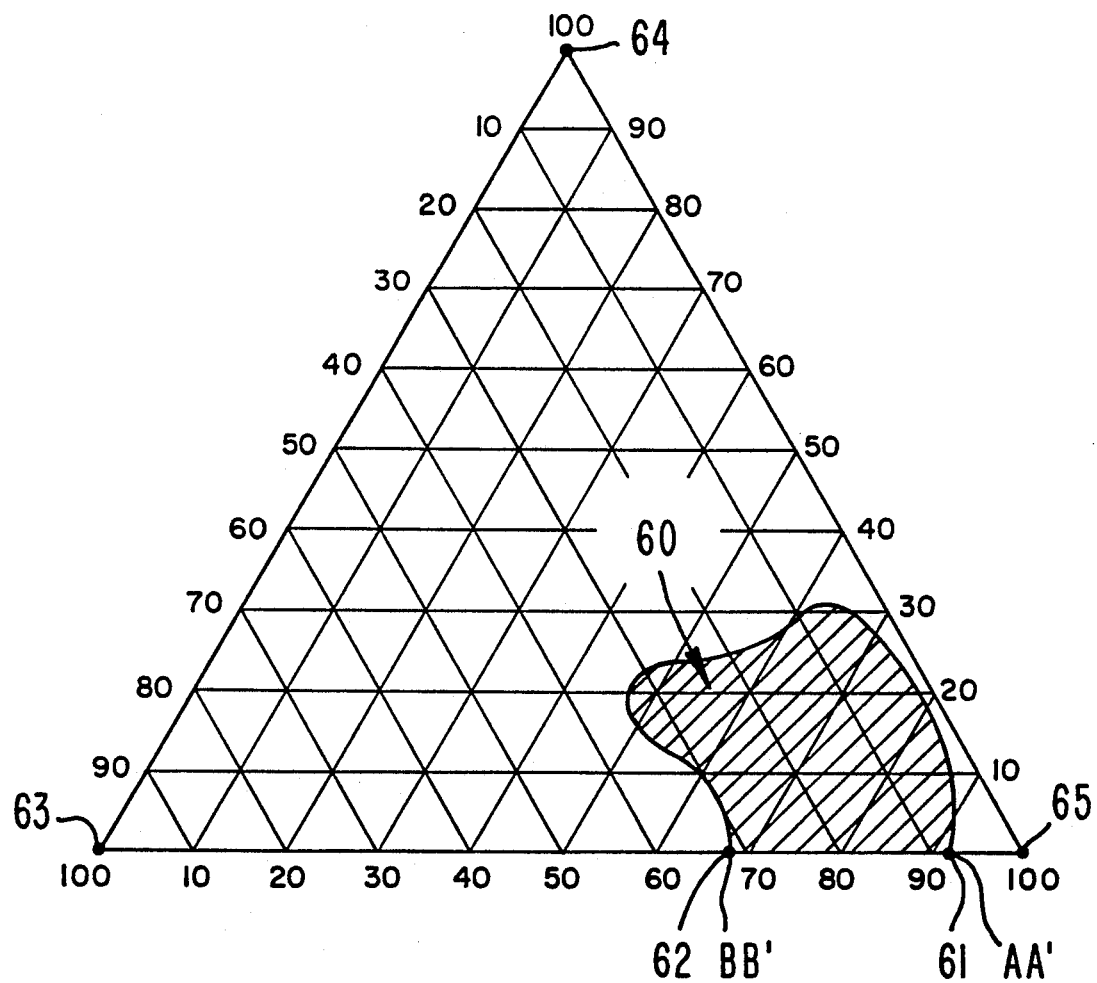
FIG. 6 is a more limited ternary phase diagram of the stable transparent oil in water microemulsion concentrates substantially in the absence of lower alkanols of our invention.

FIG. 6 is another transparent microemulsion flavor ternary phase diagram of our invention wherein the shaded area indicated by reference numeral 60 is the area covering the components of our invention. The area 60 is bounded by lines "AA'''"-"BB'''" and by the curve connecting "AA"8 and "BB'''". The end of the curve and the end of the line is indicated by reference numeral 61 at point "A'''" and is indicated by reference numeral 62 at point "BB'''". 100% Detergent (in this case CREMOPHOR ® RH 60) is indicated by reference numeral 65. 100% Mouthwash flavor is indicated by reference numeral 64. 100% Water is indicated by reference numeral 63.

FIG. 7 is another ternary phase diagram showing a specific group of transparent microemulsion flavors of our invention. The microemulsion flavor components are located within the shaded area 70 bounded by the curve connecting points "AAA" and "BBB" and bounded by the line connecting points "AAA" and "BBB". Point "AAA" is indicated by reference numeral 71. Point "BBB" is indicated by reference numeral 762. 100% Mouthwash flavor is indicated by reference numeral 74. 100% Water is indicated by reference numeral 73. 100% Detergent (in this case CREMOPHOR ® RH 40) is indicated by reference numeral 75.

The following examples are illustrative and our invention is only limited as defined according to the claims.

EXAMPLE I

The following mouthwash base is formed:

| | |
|---|---|
| Solubiliser | 0.25% |
| Spearmint Oil | 0.25% |
| Sorbitol 70% | 10.0% |
| Sodium Chloride | 0.05% |
| Sodium Saccharin | 0.03% |
| Disodium Phosphate | 0.07% |
| Citric Acid | 0.02% |
| Water | to 100%. |

The resulting mouthwash base is a microemulsion which remains clear at temperatures in the range of form about 20° C. up to about 30° C. for a period of three months.

EXAMPLE II

Objective

To develop a mouthwash microemulsion which will produce a clear solution in an alcohol-free mouthwash.

MATERIALS AND METHOD

Materials

Spearmint mouthwash flavor oil;
TWEEN ®20 ; and
Dionized water.

Method

A phased diagram using the above three components was constructed. Every region in 5-10% divisions of each component of the whole diagram was tested to create a microemulsion area. The flavor oil was first added to the TWEEN ®20 followed by water. The mixture was shaken until a clear microemulsion was formed.

Results

The shaded area is the microemulsion area.

The following mouthwash formulations are used in place of pure water:

| Ingredients | Percent |
|---|---|
| Formulation No. 1 | |
| Sorbitol | 10% |
| Sodium Citrate | 0.07% |
| Citric Acid | 0.03% |
| Sodium Saccharin | 0.04% |
| Color (1% Blue No. 1) | 0.024% |
| Sodium Benzoate | 0.15% |
| Water | 89.686% |
| Fluoride Mouthwash Formulation No. 2 | |
| Sorbitol | 10% |
| Sodium Citrate | 0.07% |
| Citric Acid | 0.03% |
| Sodium Saccharin | 0.04% |
| Color (1% Blue No. 1) | 0.022% |
| Sodium Benzoate | 0.15% |
| Sodium Fluoride | 0.05% |
| Water | 89.638% |

EXAMPLE III

Objective

To develop a mouthwash microemulsion which will produce a clear solution in alcohol-free mouthwash.

MATERIALS AND METHOD

Materials

Mouthwash flavor oil which is spearmint oil; CREMOPHOR ® RH 60 and Deionized Water.

Method

Same as that in Example II except CREMOPHOR ® RH 60 was first melted in a warm water bath before the flavor oil and water were added to it, respectively. The CREMOPHOR ® RH60 is in solid form at room temperature.

Results

The shaded area in the microemulsion region is shown in FIG. 6 and covers the components of our invention.

What is claimed is:

1. An alcohol-free transparent mouthwash consisting of an alcohol-free mouthwash base, water and a stable transparent oil-in-water microemulsion flavor concentrate consisting of:
   (i) water;
   (ii) one or more hydrophobic flavor oils; and
   (iii) one or more surfactants
in the absence of lower alkanols wherein the mixing ratio of water, oil and surfactant is defined according to the shaded area of FIG. 1A.

2. The alcohol-free mouthwash of claim 1 wherein the transparent microemulsion is defined according to the shaded area of FIG. 1B.

3. The alcohol-free mouthwash of claim 1 wherein the transparent microemulsion is defined according to the shaded area of FIG. 2.

4. The alcohol-free mouthwash of claim 1 wherein the transparent microemulsion flavor is defined according to the shaded area of FIG. 3.

5. The alcohol-free mouthwash of claim 1 wherein the transparent microemulsion flavor is defined according to the shaded area of FIG. 4.

6. The alcohol-free mouthwash of claim 1 wherein the transparent microemulsion flavor is defined according to the shaded area of FIG. 5.

7. The alcohol-free mouthwash of claim 1 wherein the transparent microemulsion flavor is defined according to the shaded area of FIG. 6.

8. The alcohol-free mouthwash of claim 1 wherein the transparent microemulsion flavor is defined according to the shaded area of FIG. 7.

9. The alcohol-free mouthwash of claim 1 wherein the transparent microemulsion flavor has a viscosity in the range of from about 70 up to about 18,000 centipoises at a temperature in the range of from about 20° C. up to 30° C.; and a refractive index in the range of from 1.4 up to 1.6 at a temperature in the range of from 20° C. up to 30° C.

* * * * *